United States Patent
Ohta et al.

(10) Patent No.: US 7,787,955 B2
(45) Date of Patent: Aug. 31, 2010

(54) MUSCLE TRAINING APPARATUS AND CONTROL METHOD THEREFOR

(75) Inventors: Atsumi Ohta, Higashikurume (JP); Nobuo Ogiwara, Ageo (JP)

(73) Assignee: Ito Co., Ltd., Tokyo (JP)

( * ) Notice: Subject to any disclaimer, the term of this patent is extended or adjusted under 35 U.S.C. 154(b) by 53 days.

(21) Appl. No.: 11/112,565

(22) Filed: Apr. 22, 2005

(65) Prior Publication Data

US 2005/0277997 A1 Dec. 15, 2005

(30) Foreign Application Priority Data

Jun. 9, 2004 (JP) ............................ P2004-171082

(51) Int. Cl.
*A61N 1/36* (2006.01)
*A61N 1/18* (2006.01)

(52) U.S. Cl. .............................. 607/48; 607/59; 607/67

(58) Field of Classification Search ............. 607/48–50, 607/59, 63–77, 46, 62, 96, 51, 52, 78, 1–3
See application file for complete search history.

(56) References Cited

U.S. PATENT DOCUMENTS

| | | | | |
|---|---|---|---|---|
| 4,919,139 A | * | 4/1990 | Brodard | 607/59 |
| 4,949,721 A | * | 8/1990 | Toriu et al. | 607/46 |
| 5,324,317 A | * | 6/1994 | Reiss | 607/67 |
| 5,350,414 A | * | 9/1994 | Kolen | 607/62 |
| 6,188,929 B1 | * | 2/2001 | Giordano | 607/59 |
| 6,564,103 B2 | * | 5/2003 | Fischer et al. | 607/59 |
| 2002/0099425 A1 | * | 7/2002 | Johnson et al. | 607/67 |
| 2003/0176901 A1 | * | 9/2003 | May | 607/68 |
| 2004/0015203 A1 | * | 1/2004 | McGraw et al. | 607/48 |

FOREIGN PATENT DOCUMENTS

| | | |
|---|---|---|
| JP | 08500751 | 1/1996 |
| JP | 08112362 | 5/1996 |
| JP | 09234252 | 9/1997 |
| JP | 2000-014803 | 1/2000 |
| JP | 2001-25510 A | 1/2001 |

(Continued)

OTHER PUBLICATIONS

Office Action corresponding to Japanese Application No. 2004-171082 dated Mar. 13, 2007.

*Primary Examiner*—Kennedy J Schaetzle
*Assistant Examiner*—Jessica Sarcione
(74) *Attorney, Agent, or Firm*—K&L Gates LLP

(57) ABSTRACT

The muscle training apparatus includes: conductors to be mounted on a body of a user; an operation section for receiving an instruction from the user; a memory section for storing a current-and-frequency-correlation data which indicates a relationship between a magnitude of an electrical stimulation signal and a supply frequency of the electrical stimulation signal; a control section for determining the supply frequency based on the magnitude of the electrical stimulation signal input from the operation section, and the current-and-frequency-correlation data; and an electrical stimulation output section for generating the electrical stimulation signal based on the magnitude of the electrical stimulation signal and the supply frequency of the electrical stimulation signal which are instructed by the control section, and generating an interference wave by providing the electrical stimulation signal to the body of the user via the conductors.

3 Claims, 4 Drawing Sheets

FOREIGN PATENT DOCUMENTS

| | | |
|---|---|---|
| JP | 2001-333990 | 12/2001 |
| JP | 3094220 | 3/2003 |
| JP | 2003-220149 | 8/2003 |
| JP | 2002143326 | 3/2007 |
| KR | 1020020004049 | 1/2002 |

* cited by examiner

CURRENT-AND-FREQUENCY-CORRELATION DATA

MUSCLE TRAINING APPARATUS AND CONTROL METHOD THEREFOR

BACKGROUND OF THE INVENTION

Priority is claimed on Japanese Patent Application No. 2004-171082, filed Jun. 9, 2004, the contents of which are incorporated herein by reference.

FIELD OF THE INVENTION

The present invention relates to a muscle training apparatus utilizing Electrical Muscle Stimulation (hereinafter "EMS") and to a control method therefor.

DESCRIPTION OF RELATED ART

A muscle training apparatus utilizing EMS is used for the purposes of muscle-building or weight reduction. The muscle training apparatus utilizing the EMS provides stimulation to muscles of a user by providing current into a body of the user via conductors. When the user's muscles experience higher stimulation by increasing current, higher effects of the exercising can be expected. However, since just increasing current causes large stimulation of a skin of the user, the user may sense pain.

Japanese Unexamined Patent Application, First Publication No. 2001-025510 discloses a technology used for such as a power sensing glove which is a man-machine interface used by a user of computers and game machines. The technology has a purpose of preventing thermal injury etc., to the user. However, in this technology, reduction or stopping of current is performed in order to ensure the safety of the user. Therefore, when the technology is applied to the muscle training apparatus, a problem of lowering the effects of the exercising arises.

SUMMARY OF THE INVENTION

In consideration of the above circumstances, an object of the present invention is to provide a muscle training apparatus which can supply higher current into a body of a user without causing excessive pain.

In order to achieve above object, the present invention provides a muscle training apparatus including: conductors to be mounted on a body of a user; an operation section for receiving an instruction from the user; a memory section for storing a current-and-frequency-correlation data which indicates a relationship between a magnitude of an electrical stimulation signal and a supply frequency of the electrical stimulation signal; a control section for determining the supply frequency based on the magnitude of the electrical stimulation signal input from the operation section, and the current-and-frequency-correlation data; and an electrical stimulation output section for generating the electrical stimulation signal based on the magnitude of the electrical stimulation signal and the supply frequency of the electrical stimulation signal which are instructed by the control section, and generating an interference wave by providing the electrical stimulation signal to the body of the user via the conductors.

According to the muscle training apparatus, since the supply frequency is changed depending on the magnitude of the electrical stimulation signal, pain of the user can be reduced while using the muscle training apparatus.

In the current-and-frequency-correlation data, the magnitude of the electrical stimulation signal may be in direct proportion to the supply frequency of the electrical stimulation signal.

In this case, since the supply frequency increases in direct proportion to the magnitude of the electrical stimulation signal, pain during using the muscle training apparatus can be reduced more effectively.

When the control section has received from the user an instruction to change the supply frequency of the electrical stimulation signal, the control section may output the instruction for changing to the control section. The control section may instruct the electrical stimulation output section to change the supply frequency of the electrical stimulation signal, based on the instruction for changing. Furthermore, the electrical stimulation output section may change the supply frequency of the electrical stimulation signal by receiving the instruction for changing from the control section.

In this case, since the user can change the supply frequency depending on the magnitude of the electrical stimulation signal, pain while using the muscle training apparatus can be decreased depending on the sensitivity of each user.

In order to achieve the above object, the present invention also provides a control method for a muscle training apparatus including: inputting an instruction from a user; determining a supply frequency which corresponds to a magnitude of an electrical stimulation signal which corresponds to the instruction, based on a current-and-frequency-correlation data which indicates a relationship between the magnitude of the electrical stimulation signal and the supply frequency of the electrical stimulation signal; generating the electrical stimulation signal based on the magnitude of the electrical stimulation signal and the supply frequency of the electrical stimulation signal; and generating an interference wave by providing the electrical stimulation signal into a body of the user.

According to the control method of the muscle training apparatus, since the supply frequency is changed depending on the magnitude of the electrical stimulation signal, pain while using the muscle training apparatus can be decreased.

In the current-and-frequency-correlation data, the magnitude of the electrical stimulation signal may be in direct proportion to the supply frequency of the electrical stimulation signal.

In this case, since the supply frequency rises in direct proportion to the magnitude of the electrical stimulation signal, pain while using the muscle training apparatus can be certainly decreased.

DETAILED DESCRIPTION OF THE INVENTION

One embodiment of the present invention will be explained below with reference to figures.

Figure 1:
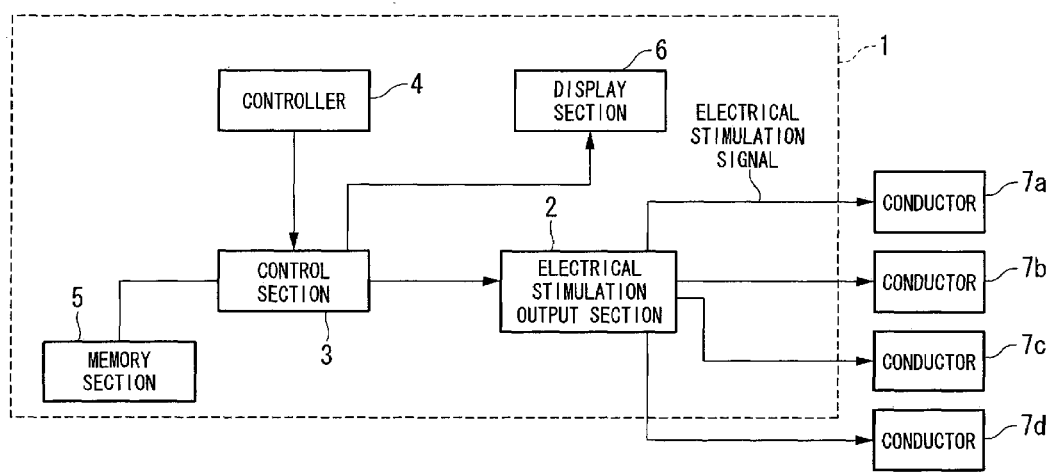
FIG. 1 is a block diagram showing a constitution of a muscle training apparatus according to one embodiment of the present invention.

FIG. 1 shows a constitution of a muscle training apparatus 1 according to the present embodiment. A control section 3 has a function for controlling the muscle training apparatus 1 (details thereof will be explained later). An electrical stimulation output section 2 generates an electrical stimulation signal based on an instruction from the control section 3, and then applies the electrical stimulation signal between conductors 7a and 7c. The electrical stimulation output section 2 also applies the electrical stimulation signal between conductors 7b and 7d.

Figure 6:
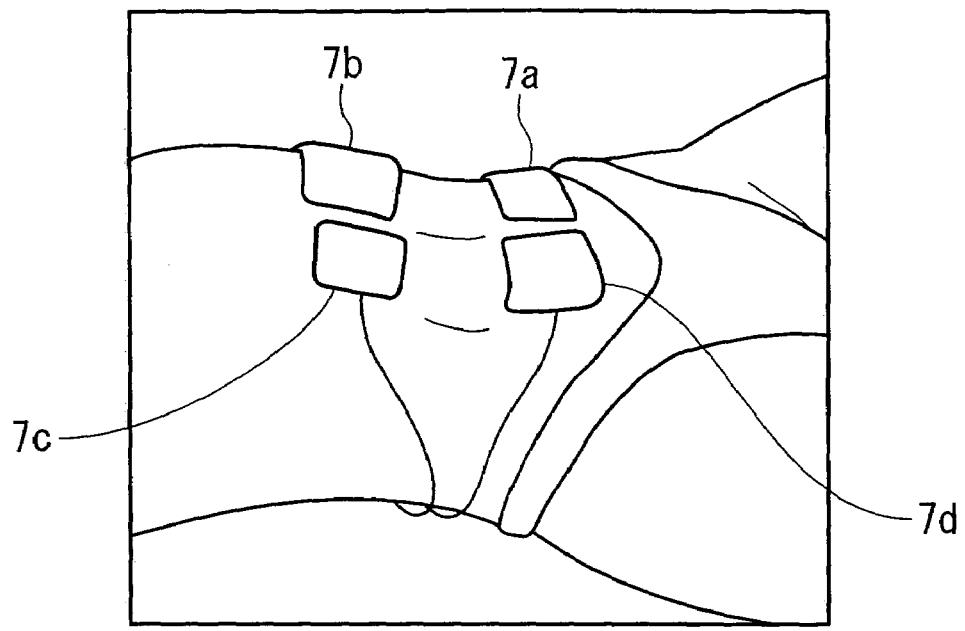
FIG. 6 is a perspective view showing conductors pasted on each position on a user's body, where a physical exercise is performed.
Figure 7:
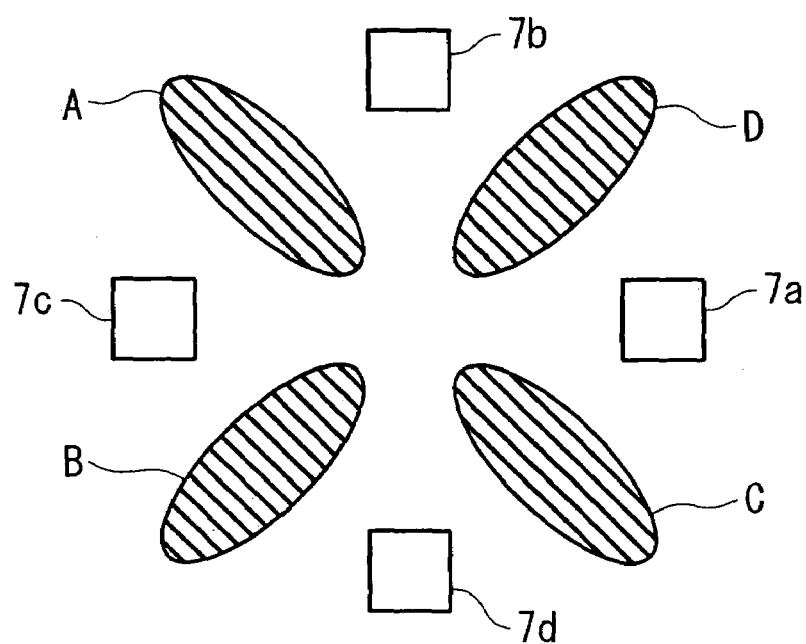
FIG. 7 is a diagram showing places of the interference waves generated by the muscle training apparatus.

The conductors 7a to 7d are pads for supplying current generated by the electrical stimulation output section 2 to a body of a user; and as shown in FIG. 6, the conductors 7a to 7d are used by pasting them on at positions which correspond to the places of the muscles which the user wishes to exercise (hereinafter "exercised part"). When the user performs exercise by pasting the conductors 7a to 7d on the exercised part as shown in FIG. 6, if, for example, current having supply frequency of 1000 Hz is applied between the conductors 7a and 7c, while current having supply frequency of 990 Hz is applied between the conductors 7b and 7d, then interference waves having frequency of 10 Hz are generated at positions A to D as shown in FIG. 7, and muscles at the positions A to D are exercised.

Figure 4:
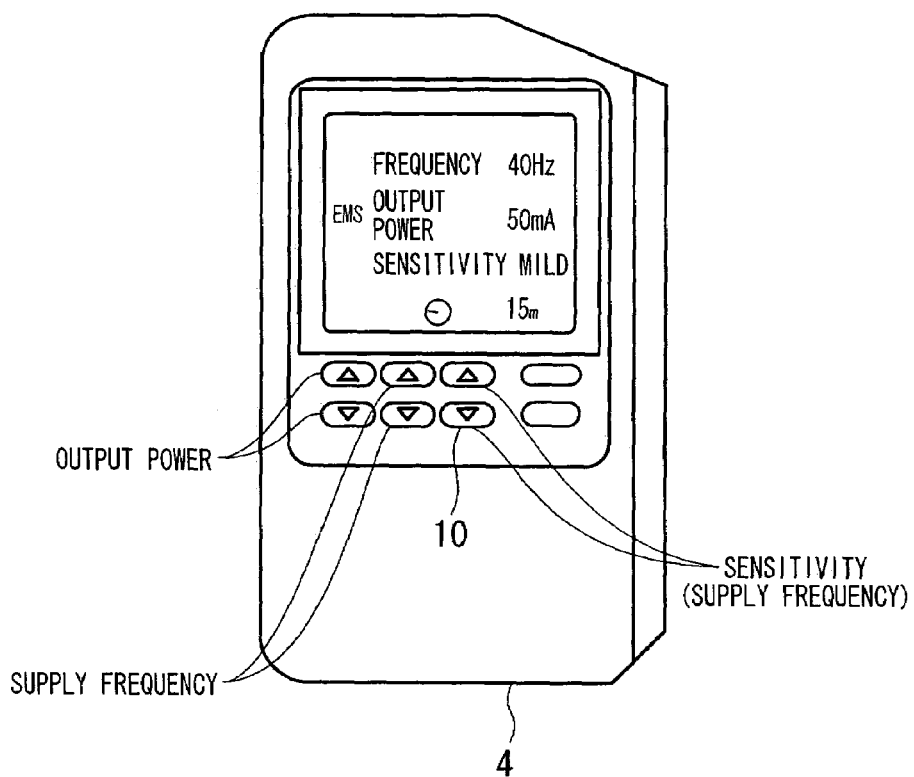
FIG. 4 is a frontal view of one example of a controller of the muscle training apparatus.

A controller (an operation section) 4 shown in FIG. 4 receives an instruction from the user of the muscle training apparatus 1, and then outputs the instruction to the control section 3. The user can set, by inputting his or her instruction into the controller 4, such that the muscle training apparatus 1 outputs an electrical stimulation signal having an output power of, for example, 10 mA to 80 mA.

A memory section 5 stores a current-and-frequency-correlation data (refer to FIG. 2) which indicates a relationship between the magnitude of the electrical stimulation signal and the supply frequency of the electrical stimulation signal. The supply frequency of the current-and-frequency-correlation data indicates an actual frequency of the electrical stimulation signal generated by the electrical stimulation output section 2.

A display section 6 displays the magnitude of the electrical stimulation signal output from the muscle training apparatus 1, etc., based on an output from the control section 3.

Figure 3:
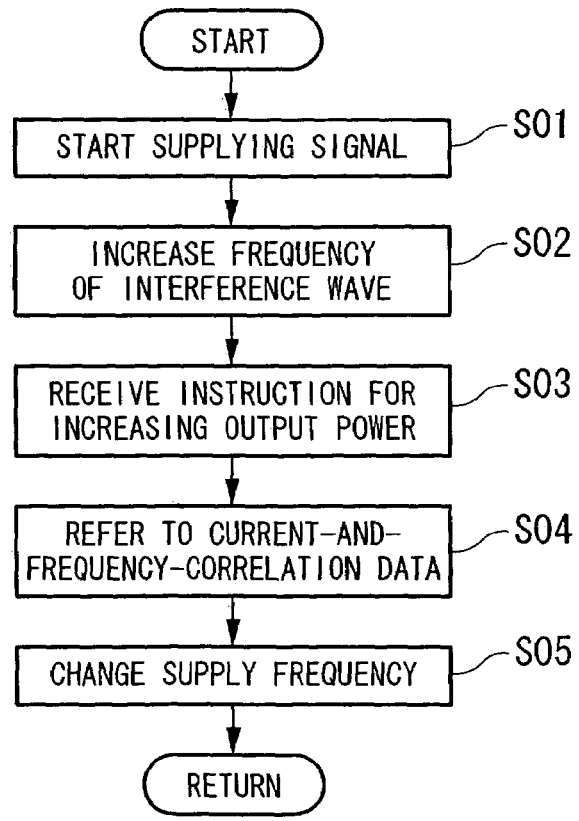
FIG. 3 is a flowchart showing a control process of the muscle training apparatus.

Next, an operation of the muscle training apparatus 1 will be explained below. FIG. 3 shows a process to be performed in the muscle training apparatus 1.

Firstly, the user of the muscle training apparatus 1 pastes the conductors 7a to 7d on the exercised part of his or her body, and then inputs an instruction for starting the exercise, to the controller 4.

Figure 2:
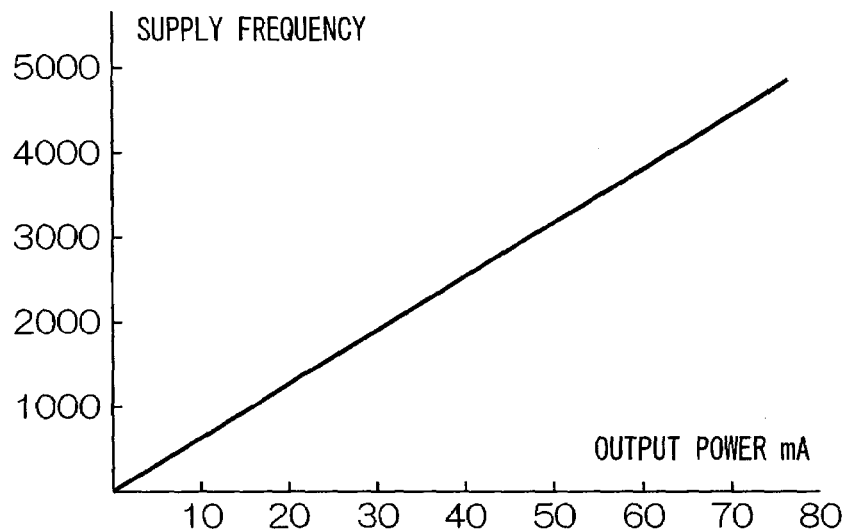
FIG. 2 is a graph showing a relationship between supply frequency and the magnitude of electrical stimulation signal output from the muscle training apparatus. In the graph, a horizontal axis shows output power, while a vertical axis shows the supply frequency.

The control section 3 of the muscle training apparatus 1 receives the instruction from the user via the controller 4, and then reads the above-mentioned current-and-frequency-correlation data shown in FIG. 2, from the memory section 5. Then, the control section 3 decides that current of the weakest level (the weakest magnitude) should be supplied into the body of the user since the current state is at the beginning of the exercising. Furthermore, the control section 3 outputs the followings (i) to (iii) to the electrical stimulation output section 2. That is, (i) the weakest current of "10 mA" based on the current-and-frequency-correlation data, (ii) the supply frequency of "600 Hz" which can be obtained from the current-and-frequency-correlation data as the corresponding supply frequency with respect to the current of "10 mA", and (iii) minimum value of "0 Hz" being a minimum value of the interference wave which is actually applied to the muscles of the user. As explained above, the control section 3 instructs the electrical stimulation output section 2 of start supplying current (in step S01 of FIG. 3). Furthermore, control section 3 sends the current status (i.e., current is 10 mA and the frequency of the interference wave is 0 Hz) to the display section 6 for displaying it. Then, the control section 3 waits for the next instruction from the user.

Following the instruction from the control section 3, the electrical stimulation output section 2 generates an electrical stimulation signal having current of 10 mA and the supply frequency of 600 Hz, and then supplies the electrical stimulation signal to the conductors 7a to 7d. At this time, since the supply frequencies of the electrical stimulation signals transmitted to the conductors 7a to 7d from the electrical stimulation output section 2 are the same each other, the interference waves will not be generated within the body of the user. Moreover, the electrical stimulation signal generated by the electrical stimulation output section 2 does not start from current of 10 mA and the supply frequency of 600 Hz; however, the electrical stimulation signal starts from current of 0 mA and the supply frequency of 0 Hz, and then gradually increases to current of 10 mA and the supply frequency of 600 Hz within a predetermined time.

Next, a case in which the user inputted the controller 4 for increasing the frequency of the interference wave to 10 Hz, will be explained below.

The control section 3 receives the above-mentioned input from the user via the controller 4, and if the control section 3 has decided that there is no need to increase the supply frequency in order to increase the interference wave to 10 Hz, then the control section 3 sends a signal for increasing the frequency of the interference wave to 10 Hz, to the electrical stimulation output section 2 (in step S02 of FIG. 3). In addition, the control section 3 outputs the current status (i.e., current is 10 mA and the frequency of the interference wave is 10 Hz) to the display section 6 for displaying it. Then the controller 3 waits for the next instruction from the user.

Following an instruction from the control section 3, the electrical stimulation output section 2 changes the current which has been currently supplied, within a predetermined time. That is, the supply frequency of the electrical stimulation signals which has been currently supplied to the conductors 7b and 7d are decreased to 590 Hz by gradually decreasing 10 Hz, while maintaining the supply frequency of the electrical stimulation signals which has been currently supplied to the conductors 7a and 7c at 600 Hz. The conductors 7a to 7d receive the electrical stimulation signals and supply the electrical stimulation signals to the exercised parts of the user. As the result, the body of the user senses the interference waves, and thereby starting the exercise.

Next, a case in which the user inputted an instruction into the controller 4 for increasing current to 30 mA, will be explained below. If the control section 3 received the instruction from the user via the controller 4 (in step S03 of FIG. 3), then the control section 3 refers to the above-mentioned current-and-frequency-correlation data (in step S04 of FIG. 3), and instructs to the electrical stimulation signal output section 2 in order to increase the output power by outputting current of 30 mA and the supply frequency of 2000 Hz to the electrical stimulation signal output section 2, and thereby instructs increasing the output power. In addition, the control section 3 outputs the current status (i.e., current is 30 mA and the frequency of the interference wave is 10 Hz) to the display section 6 for displaying it. Then the controller 3 waits for the next instruction from the user.

When each size of the conductors 7a to 7d is termed as "T" while each of the supply frequency applied to the conductors 7a to 7d is termed as "C", the skin resistance of a human can be defined as "$1/(2\pi TC)$". Therefore, the skin resistance can be decreased by increasing the supply frequency C along with the rise of the output power of the electrical stimulation signal. Moreover, it is known that, for example, increasing the supply frequency from 100 Hz to 1000 Hz results in much milder stimulation to the skin than the case in which the supply frequency is increased from 10 Hz to 100 Hz, although both cases are the same in that the increase is 10 times. In the above-mentioned processes by the control section 3, since the supply frequency is increased from 600 Hz to 2000 Hz, much milder stimulation to the skin can be obtained than the case in which the supply frequency is increased from 10 Hz to 100 Hz.

If the electrical stimulation output section 2 receives an instruction from the control section 3, then the electrical stimulation output section 2 transmits a signal for gradually increasing, within a predetermined time, the output power and the supply frequency of the electrical stimulation signal to be generated, to the conductors 7a to 7d (in step S05 of FIG. 3). At this time, in a manner similar to that as explained above, the electrical stimulation output section 2 provides a difference between (i) the supply frequency of the electrical stimulation signal supplied between the conductors 7a and 7c, and (ii) the supply frequency of the electrical stimulation signal supplied between the conductors 7b and 7d. After this process, the control section 3 changes the frequencies and/or the output powers of the interference waves depending on a request from the user.

While preferred embodiment of the invention has been described and illustrated above, it should be understood that this is exemplary of the invention and is not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

For example, the present invention may be applied to treatment devices for easing or blocking pain in muscles In this case, since higher current can be supplied into a body of a patient without severe pain in the skin of the patient, higher curative effect can be expected.

In the present embodiment, a case is described where the EMS is generated by using a four-electrodes-interference method in which the EMS is generated by four conductors (i.e., the conductors 7a to 7d). However, the number of the conductors is not limited to four, and may be, for example, 6 or more. In the case in which the number of the conductors is increased, further high curative effect can be expected since an area of the interference waves generated by the conductors can be broader.

In addition, in the present embodiment, a case is described where the electrical stimulation signal generated by the electrical stimulation output section 2 is a signal shown in FIG. 2, in which the supply frequency increases in direct proportion to the output power. However, the type of the electrical stimulation signal is not limited to the signal shown in FIG. 2, and may be a signal in which the supply frequency is changeable by the user's instruction. For example, the user may increase or decrease the magnitude of stimulation by operating the controller shown in FIG. 4. In this case, if the user felt pain in his or her skin, the user depresses an inverted-triangle-mark button 10 of the controller 4 shown in FIG. 4. This operation is detected by the control section 3, and the control section 3 sends an instruction to the electrical stimulation output section 2 for increasing the supply frequency. As the result, the supply frequency is increased and the user's pain can be decreased.

When the electrical stimulation signal having the same supply frequency and the same output power is applied, some may feel pain while others do not. Therefore, the user who is sensitive to the pain can decrease the pain by setting the supply frequency higher while using the muscle training apparatus 1.

In addition, in order that the user can enter the meaning indicated on the display section 6 immediately, wordings such as "HARD", "MILD", and etc., or symbols such as face marks, etc., may be displayed instead of displaying the number of the supply frequency.

In addition, in the present embodiment, a case is described where the muscle training apparatus 1 does not include a function for performing "warming up" which is usually performed before the exercising or "cool down" which is usually performed after the exercising; however, the muscle training apparatus 1 may include the function. In this case, damage to muscles due to a rapid exercise while performing exercise using the muscle training apparatus 1 can be effectively prevented.

Figure 5:
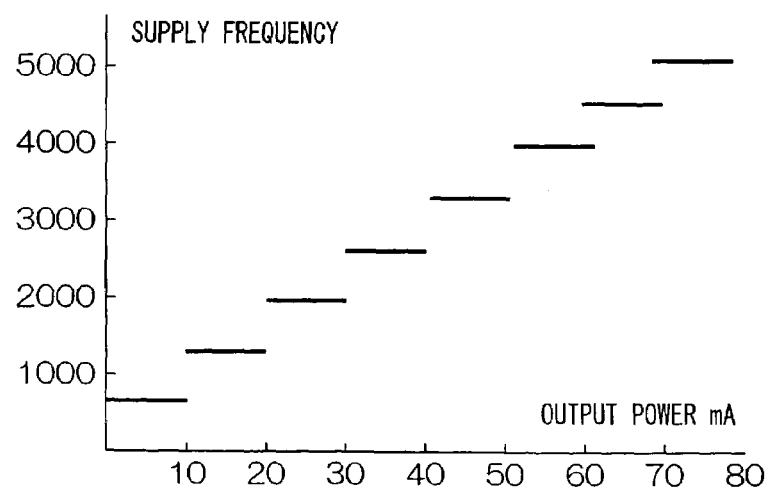
FIG. 5 is a graph showing a modified example of the relationship between supply frequency and the magnitude of electrical stimulation signal output from the muscle training apparatus. In the graph, a horizontal axis shows output power, while a vertical axis shows the supply frequency.

Furthermore, in the present embodiment, a case is described where the electrical stimulation signal generated by the electrical stimulation output section 2 is a signal shown in FIG. 2, in which the supply frequency increases in direct proportion to the output power. However, the type of the electrical stimulation signal is not limited to the signal shown in FIG. 2, and may be a signal shown in FIG. 5, in which the supply frequency increases step-by-step for each of the predetermined output ranges. In this case, a configuration of the muscle training apparatus 1 becomes simple, and thus, the muscle training apparatus 1 can be smaller and inexpensive.

What is claimed is:

1. A muscle training apparatus comprising:
    conductors to be mounted on a body of a user;
    an operation section for receiving a magnitude of an electrical stimulation signal or a magnitude of an interference wave frequency from the user;
    a memory section for storing a current-and-frequency-correlation data which correlates the magnitude of the electrical stimulation signal with
    a supply frequency of the electrical stimulation signal;
    a control section for determining the supply frequency based on
        the magnitude of the electrical stimulation signal or
        the magnitude of the interference wave frequency input to the operation section by the user, and
        the current-and-frequency-correlation data; and
    an electrical stimulation output section for
        generating the electrical stimulation signal based on
            the magnitude of the electrical stimulation signal,
            the magnitude of the interference wave frequency, and
            the supply frequency of the electrical stimulation signal which are instructed by the control section, and
        generating an interference wave by providing the electrical stimulation signal to the body of the user via the conductors,
    wherein in the current-and-frequency-correlation data, in which the magnitude of the electrical stimulation signal is correlated with the supply frequency of the electrical stimulation signal in an equal-interval graph with the magnitude of the electrical stimulation signed as a horizontal axis and the supply frequency as a vertical axis, the magnitude of the electrical stimulation signal is in direct proportion to the supply frequency of the electrical stimulation signal for an entire supply frequency band range more than or equal to 0 Hz, and wherein the electrical stimulation signal or the supply frequency of the electrical stimulation signal does not change along with changes in time.

2. The muscle training apparatus according to claim 1, wherein the operation section is configured to receive instruction for changing the supply frequency of the electrical stimulation signal from the user, such that the operation section outputs the instruction for changing to the control section;

the control section instructs the electrical stimulation output section to change the supply frequency of the electrical stimulation signal, based on the instruction for changing; and the electrical stimulation output section changes the supply frequency of the electrical stimulation signal by receiving the instruction for changing from the control section.

3. A control method of a muscle training apparatus comprising:

inputting an instruction from a user;

determining a supply frequency which corresponds to a magnitude of an electrical stimulation signal which corresponds to the instruction, based on a current-and-frequency-correlation data which correlates the magnitude of the electrical stimulation signal with a supply frequency of the electrical stimulation signal;

generating the electrical stimulation signal based on the magnitude of the electrical stimulation signal and the supply frequency of the electrical stimulation signal; and generating an interference wave by providing the electrical stimulation signal into a body of the user, wherein in the current-and-frequency-correlation data, in which the magnitude of an electrical stimulation signal is correlated with the supply frequency of the electrical stimulation signal in an equal-interval graph with the magnitude of the electrical stimulation signal as a horizontal axis and the supply frequency as a vertical axis, the magnitude of the electrical stimulation signal is in direct proportion to the supply frequency of the electrical stimulation signal for an entire supply frequency band range more than or equal to 0 Hz, and wherein the electrical stimulation signal or the supply frequency of the electrical stimulation signal does not change along with changes in time.

* * * * *